(12) United States Patent
Cutforth et al.

(10) Patent No.: US 12,347,101 B2
(45) Date of Patent: Jul. 1, 2025

(54) METHOD AND APPARATUS FOR PRODUCING CONTRAINED MEDICAL IMAGE DATA

(71) Applicant: CANON MEDICAL SYSTEMS CORPORATION, Otawara (JP)

(72) Inventors: Murray Cutforth, Edinburgh (GB); Marco Razeto, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 463 days.

(21) Appl. No.: 17/658,096

(22) Filed: Apr. 6, 2022

(65) Prior Publication Data
US 2023/0326011 A1 Oct. 12, 2023

(51) Int. Cl.
*G06T 7/00* (2017.01)
*A61B 6/00* (2024.01)
(Continued)

(52) U.S. Cl.
CPC .......... *G06T 7/0012* (2013.01); *A61B 6/4085* (2013.01); *A61B 6/4441* (2013.01);
(Continued)

(58) Field of Classification Search
CPC .............. G06T 7/0012; G06T 7/10; G06T 2207/10064; G06T 2207/10081;
(Continued)

(56) References Cited

U.S. PATENT DOCUMENTS 10,140,544 B1 11/2018 Zhao et al.
2005/0165292 A1 7/2005 Simon et al.
(Continued)

FOREIGN PATENT DOCUMENTS

CN 109087306 A 12/2018
CN 109146872 A 1/2019
(Continued)

OTHER PUBLICATIONS

R. Kimura et al. "Virtual Digital Subtraction Angiography Using Multizone Patch-based U-Net", Physical and Engineering Sciences in Medicine, 1-11, 2020, pp. 1305-1315.
(Continued)

*Primary Examiner* — Matthew C Bella
*Assistant Examiner* — Jinsu Hwang
(74) *Attorney, Agent, or Firm* — Oblon, McClelland, Maier & Neustadt, L.L.P.

(57) ABSTRACT

An apparatus for producing constrained medical image data, the apparatus including processing circuitry configured to: receive medical image data that includes or is obtained from scan data representing an anatomical region in which a sub-region is enhanced; predict, using a trained model, mask data from the medical imaging data, wherein the mask data is representative of the anatomical region without enhancement of the sub-region; and predict, using the trained model or a further trained model, subtraction data from the same medical image data, the subtraction data being representative of the same anatomical region, and the processing circuitry being further configured to apply at least one constraint to obtain constrained subtraction data.

19 Claims, 4 Drawing Sheets

(51) Int. Cl.
 *A61B 6/40* (2024.01)
 *G06T 7/10* (2017.01)
(52) U.S. Cl.
 CPC ...... *G06T 7/10* (2017.01); *G06T 2207/10064* (2013.01); *G06T 2207/10081* (2013.01); *G06T 2207/10088* (2013.01); *G06T 2207/20084* (2013.01); *G06T 2207/30101* (2013.01)
(58) Field of Classification Search
 CPC . G06T 2207/10088; G06T 2207/20084; G06T 2207/30101; A61B 6/4085; A61B 6/4441
 See application file for complete search history.

(56) References Cited

U.S. PATENT DOCUMENTS

| | | | |
|---|---|---|---|
| 2015/0139514 A1* | 5/2015 | Mohr | G06T 5/50 382/131 |
| 2017/0270687 A1 | 9/2017 | Manhart | |
| 2018/0116620 A1 | 5/2018 | Chen et al. | |
| 2018/0374209 A1 | 12/2018 | Patil et al. | |
| 2019/0046145 A1 | 2/2019 | Leghissa et al. | |
| 2020/0273217 A1 | 8/2020 | Kaethner et al. | |
| 2020/0320751 A1 | 10/2020 | Siemionow et al. | |
| 2020/0349712 A1 | 11/2020 | Siemionow et al. | |
| 2020/0410687 A1 | 12/2020 | Siemionow et al. | |
| 2021/0049756 A1 | 2/2021 | He et al. | |
| 2022/0091568 A1* | 3/2022 | Kong | G05B 13/048 |
| 2023/0263493 A1* | 8/2023 | Cantrell | G06T 11/006 382/131 |

FOREIGN PATENT DOCUMENTS

| | | |
|---|---|---|
| CN | 110163809 A | 8/2019 |
| CN | 111353989 A | 6/2020 |
| CN | 111383259 A | 7/2020 |
| CN | 111755104 A | 10/2020 |
| CN | 111815766 A | 10/2020 |
| CN | 112053414 A | 12/2020 |
| KR | 10-2020-0093502 A | 8/2020 |
| WO | WO 2018/155765 A1 | 8/2018 |
| WO | WO 2020/050635 A1 | 3/2020 |
| WO | WO 2020/122672 A1 | 6/2020 |
| WO | WO 2021/025461 A1 | 2/2021 |
| WO | WO 2021/257906 A1 | 12/2021 |

OTHER PUBLICATIONS

J.C. Montoya et al., "3D Deep Learning Angiography (3D-DLA) from C-arm Conebeam CT", American Journal of Neuroradiology, Mar. 2018, pp. 1-7.

Extended European Search Report issued Aug. 9, 2023 in European Patent Application No. 23166581.1, 7 pages.

* cited by examiner

US 12,347,101 B2

METHOD AND APPARATUS FOR PRODUCING CONTRAINED MEDICAL IMAGE DATA

FIELD

Embodiments described herein relate generally to an image processing method and apparatus, for example a method and apparatus for predicting subtraction data from contrast-enhanced data.

BACKGROUND

Medical imaging techniques that can produce medical imaging data using any of a variety of imaging modalities are widely used for imaging or diagnostic purposes.

It is known to perform an angiography procedure in which a contrast agent is introduced into blood vessels of a patient and the blood vessels are imaged using X-ray imaging. The contrast agent increases the intensity of the vessel lumen as viewed in an X-ray image.

The angiography procedure may comprise, for example, 2D fluoroscopy or 3D rotational angiography. The angiography procedure may be performed, for example, while planning an operation or during an operation.

An imaging data set that is obtained using a contrast agent may be referred to as a contrast volume or contrast-enhanced volume. An imaging data set that is obtained without the contrast agent present may be referred to as a mask volume. Vessels are less visible in the mask volume than in the contrast volume due to the absence of contrast agent.

A subtraction volume may be obtained by subtracting a mask volume and a contrast volume that are representative of the same anatomy. For example, the subtracting may comprise subtracting intensities of the mask volume from intensities of the contrast volume at each corresponding location in the mask volume and contrast volume. The subtraction process may remove features that are common to the contrast volume and the mask volume (for example, bone and soft tissue) and leave only the parts of the contrast volume that have been enhanced by the contrast agent.

The subtraction volume may also be referred to as a digital subtraction angiography (DSA) volume.

FIG. 1 is a flow chart illustrating in overview a subtraction process. Volumes are illustrated in FIG. 1 by images that are rendered from those volumes. The images are intended to indicate whether each volume is a mask volume, a contrast volume or a subtraction volume, and do not correspond to images produced in a real subtraction process.

A contrast volume 2 and a mask volume 4 are obtained for the same anatomy. A registration and subtraction process 6 is performed in which the contrast volume and mask volume are registered to each other and a subtraction is performed. The subtraction subtracts intensities of the mask volume from intensities of the contrast volume. The subtraction process 6 results in a DSA volume 8. In images rendered from the DSA volume 8, vessels become more visible than they are in the contrast volume, since bone and soft tissue are removed.

In recent years it has been proposed to use machine learning to predict a mask volume and a DSA volume from a single contrast volume. Such techniques may be referred to as Maskless DSA. An aim of Maskless DSA is to predict the DSA volume from the contrast-enhanced volume without acquiring a mask volume.

For example, one or more convolutional neural networks (CNNs) may be trained to predict the mask volume and DSA volume from the contrast volume. A deep CNN may be trained to directly predict intensities of a DSA.

FIG. 2 is a flow chart illustrating in overview a maskless DSA method. A contrast volume 2 is input into a CNN 10. The CNN outputs a DSA volume 12.

It has been found that presenting an output of a deep CNN to a clinician may be problematic in some circumstances. For example, it has been found that in some circumstances the deep CNN may generate image features that do not exist in reality. The generating of non-existent features may be described as the model hallucinating such non-existent features. Reducing or eliminating such non-existent image features may require a prohibitive amount of model testing.

In some circumstances, features present in the contrast-enhanced volume may not be present in the predicted DSA and mask. A feature present in the contrast volume may appear in neither the DSA predicted by the CNN nor the mask predicted by the CNN. Such features may be considered to have disappeared in the predicted DSA and mask.

In some circumstances, the CNN may have great difficulty in distinguishing between metal objects and enhanced vessels, where the enhanced vessels are enhanced by the presence of contrast agent. Metal objects should be masked, while enhanced vessel should not be masked. Examples of metal objects that may appear in an angiography image of the brain include metal objects implanted during neurosurgery, for example screws or clips.

BRIEF DESCRIPTION OF THE DRAWINGS

Embodiments are now described, by way of non-limiting example, and are illustrated in the following figures, in which.

DETAILED DESCRIPTION

Certain embodiments provide a medical image processing apparatus comprising processing circuitry configured to: receive medical image data that comprises or is obtained from scan data representing an anatomical region in which contrast agent is present; predict, using a trained model, mask data from the medical imaging data, wherein the mask data is representative of the anatomical region without the contrast agent; and predict, using the trained model or a further trained model, subtraction data from the same medical image data, wherein the subtraction data is representative of the same anatomical region; wherein the processing circuitry is further configured to apply at least one constraint to obtain constrained subtraction data.

Certain embodiments provide a medical image processing method comprising: receiving medical image data that comprises or is obtained from scan data representing an anatomical region in which contrast agent is present; predicting, using a trained model, mask data from the medical imaging data, wherein the mask data is representative of the anatomical region without the contrast agent; predicting, using the trained model or a further trained model, subtraction data from the same medical image data, wherein the subtraction data is representative of the same anatomical region; and applying at least one constraint to obtain constrained subtraction data.

Figure 3:
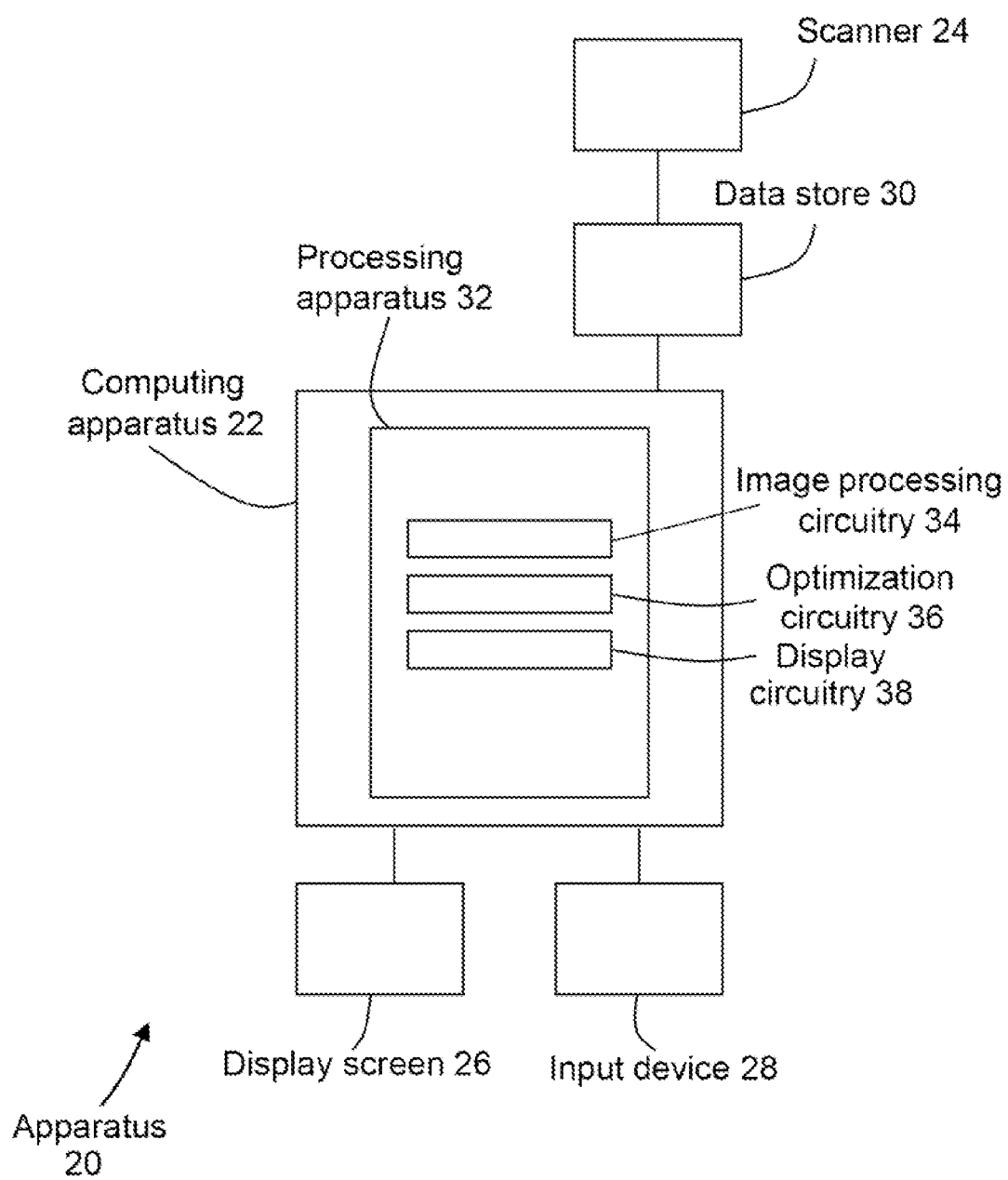
FIG. 3 is a schematic illustration of an apparatus in accordance with an embodiment.

A medical image processing apparatus 20 according to an embodiment is illustrated schematically in FIG. 3.

The medical image processing apparatus 20 comprises a computing apparatus 22, in this case a personal computer (PC) or workstation, which is connected to a scanner 24 via a data store 30.

The medical image processing apparatus 20 further comprises one or more display screens 26 and an input device or devices 28, such as a computer keyboard, mouse or trackball.

In the present embodiment, the scanner 24 is an X-ray scanner which is configured to obtain X-ray images, for example 2D fluoroscopy or 3D rotational angiography images. The X-ray scanner may be a cone-beam C-arm scanner. The scanner 24 is configured to generate image data that is representative of at least one anatomical region of a patient or other subject. The image data comprises a plurality of voxels each having a corresponding data value. In the present embodiment, the data values are representative of X-ray intensity. The scanner is used to obtain a contrast volume in which blood vessels are enhanced by presence of a contrast agent.

In other embodiments, the scanner 24 may be configured to obtain two-, three- or four-dimensional image data in any imaging modality. For example, the scanner 24 may comprise a magnetic resonance (MR) scanner, computed tomography (CT) scanner, cone-beam CT scanner, positron emission tomography (PET) scanner, X-ray scanner, or ultrasound scanner. Any suitable method may be used to enhance a sub-region of an anatomical region, for example to enhance vessels, one or more organs, or at least part of a digestive tract.

In the present embodiment, image data sets obtained by the scanner 24 are stored in data store 30 and subsequently provided to computing apparatus 22. In an alternative embodiment, image data sets are supplied from a remote data store (not shown). The data store 30 or remote data store may comprise any suitable form of memory storage. In some embodiments, the medical image processing apparatus 20 is not coupled to any scanner.

Computing apparatus 22 comprises a processing apparatus 32 for processing of data. The processing apparatus comprises a central processing unit (CPU) and Graphical Processing Unit (GPU). The processing apparatus 32 provides a processing resource for automatically or semi-automatically processing medical image data sets. In other embodiments, the data to be processed may comprise any image data, which may not be medical image data.

The processing apparatus 32 includes image processing circuitry 34 for processing image data using a trained model to obtain predicted volumes, optimization circuitry 36 for performing an optimization procedure on the predicted volumes to obtain constrained volumes, and display circuitry 38 for displaying images obtained from the constrained volumes.

In the present embodiment, the circuitries 34, 36, 38 are each implemented in the CPU and/or GPU by means of a computer program having computer-readable instructions that are executable to perform the method of the embodiment. In other embodiments, the circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 3 for clarity.

Figure 4:
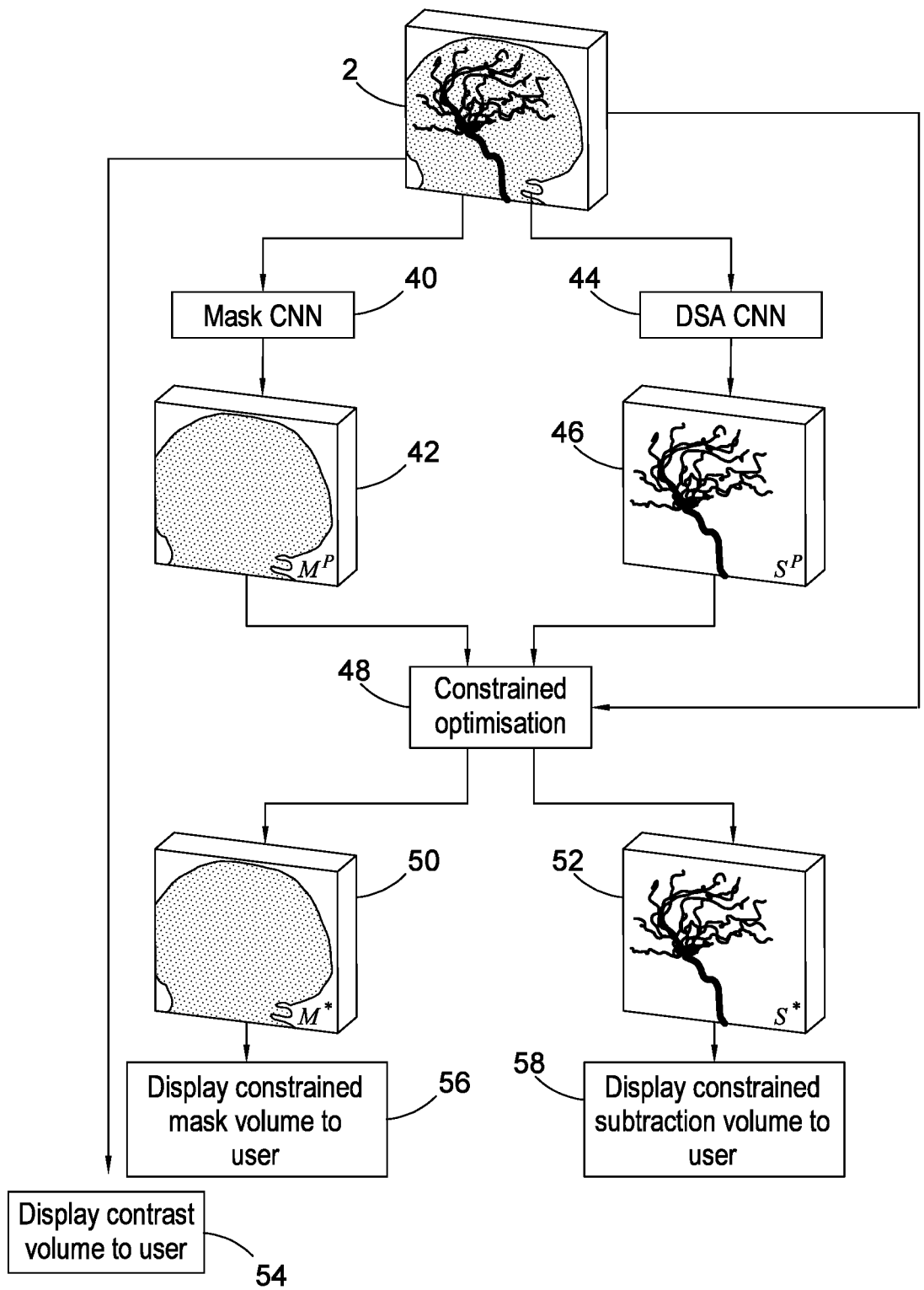
FIG. 4 is a flow chart illustrating in overview a maskless DSA method in accordance with an embodiment.

FIG. 4 is a flow chart illustrating in overview a method of an embodiment. Apparatus is configured to perform the method of FIG. 4. In other embodiments, any suitable apparatus or apparatuses may be used to perform the method of FIG. 4.

At the start of the method of FIG. 4, the image processing circuitry 34 receives a contrast volume 2. The contrast volume 2 comprises angiographic data. In the embodiment of FIG. 4, the contrast volume is a volumetric data set that is obtained from 3D rotational angiography and comprises data that is representative of the head of a patient. Blood vessels of the head have been enhanced in the contrast scan by the introduction of a contrast agent. The blood vessels form an enhanced sub-region within the contrast volume.

In other embodiments, the angiographic data may be 2D data. The angiographic data may be obtained from 2D fluoroscopy. In other embodiments, the angiographic data may be CT data. In further embodiments, the contrast volume 2 may comprise or be obtained from scan data obtained using any suitable contrast-enhanced scan procedure or other form of enhancement. For example, the contrast volume may be obtained using magnetic resonance angiography (MRA). In some embodiments, blood is enhanced, for example to show the blood vessels. In some embodiments, contrast agent may accumulate in an organ of interest to image a specific type of soft tissue. In other embodiments, a contrast agent may be used to enhance the digestive tract, for example in a barium swallow.

The image processing circuitry 34 inputs the contrast volume 2 to a mask CNN 40. The mask CNN 40 may be any suitable CNN, for example a 3D residual U-net. The mask CNN 40 is trained to predict a mask volume given an input of a contrast volume. The mask CNN 40 outputs a predicted mask volume 42. The predicted mask volume 42 is intended to represent the head of the patient when contrast is not present. Parts of the head that do not form part of the contrast-enhanced vessels are intended to be included in the mask volume. Any metal objects present in the head are intended to be included in the mask volume. However, it is possible that in some circumstances the predicted mask volume 42 may contain errors. For example, features that do not exist in the contrast volume may be predicted by the mask CNN, or the mask CNN may omit features of the contrast volume that should be included in the mask volume.

The image processing circuitry 34 inputs the contrast volume 2 to a DSA CNN 44. The DSA CNN 44 may be any suitable CNN, for example a 3D residual U-net. In the embodiment of FIG. 4, the DSA CNN 44 is independent of the mask CNN 40. The DSA CNN 44 is trained to predict a subtraction volume given an input of a contrast volume. The DSA CNN 44 outputs a predicted subtraction volume 46. The predicted subtraction volume 46 is intended to represent the contrast-enhanced vessels of the head of the patient while removing bone and soft tissue. It is possible that in some circumstances the predicted subtraction volume 46 may contain errors. For example, features that do not exist in the contrast volume may be predicted by the DSA CNN 44, or the DSA CNN 44 may omit features of the contrast volume that should be included in the DSA volume. In some circumstances, there may be one or more features of the contrast volume that have not been included in either the predicted mask volume 42 or the predicted subtraction volume 46.

In other embodiments, any suitable method may be used to obtain predicted mask volume 42 and predicted subtraction volume 46 from contrast volume 2. Any suitable trained model or models may be used to obtain the predicted mask volume 42 and the predicted subtraction volume 46. In some embodiments, the models may not be CNNs. In some embodiments, the models may be generative models. For example, generative models from a conditional generative adversarial network may be used to obtain the predicted mask volume 42 and the predicted subtraction volume 46.

The predicted mask volume 42 obtained from the mask CNN 40 and the predicted subtraction volume 46 obtained from the DSA CNN 44 may be described as initial predictions or as intermediate predictions.

The predicted mask volume 42 and predicted subtraction volume 46 are passed to the optimization circuitry 36. The optimization circuitry 36 performs a constrained optimization procedure 48 using the predicted mask volume 42 and predicted subtraction volume 46 as inputs.

In the present embodiment, the constrained optimization procedure comprises an optimization procedure having two constraints.

A first constraint is that adding a mask volume derived from a contrast volume and a subtraction volume derived from a contrast volume should result in the original contrast volume. For each of a plurality of locations within the volumes, an intensity for that location in the predicted mask volume and an intensity for that location in the predicted subtraction volume should add to give the intensity for that location in the contrast volume. In the present embodiment, the first constraint is applied to voxelwise addition. An intensity value for a given voxel of the contrast volume must equal the sum of the intensity value for that voxel in the mask volume and the intensity value for that voxel in the subtraction volume.

A second constraint is that all intensity values for every location in each of the volumes should be non-negative. In the present embodiment, each voxel of the mask volume must have a non-negative value for intensity and each voxel of the subtraction volume must have a non-negative value for intensity. In other embodiments, there exists a predetermined range of intensity values. Intensity values of the volumes are constrained such that all intensity values in each volume are within the predetermined range. A minimum value for intensity may be determined, for example a minimum value that it is possible to obtain in a real volume acquisition or a minimum value found in the contrast volume. A maximum value for intensity may be determined, for example a maximum value that it is possible to obtain in a real volume acquisition or a maximum value found in the contrast volume. The minimum value and maximum value for intensity may be used to set the predetermined range that all predicted intensity values must fall within.

The constrained optimization procedure 48 is designed to compute mask and subtraction volumes which are as close as possible to the predicted mask volume 42 predicted by the mask CNN 40 and the predicted subtraction volume 46 predicted by the DSA CNN 44, while also satisfying the first and second constraints.

We now describe the constrained optimization procedure according to the embodiment of FIG. 4. In other embodiments, a different optimization procedure may be used.

Inputs to the constrained optimization procedure are the contrast volume 2 which is denoted as C, the predicted mask volume 42 which is denoted as $M^P$, and the predicted subtraction volume 46 which is denoted as $S^P$. Typically, $C \in \mathbb{R}^{512^3}$ and $M^P$ and $S^P$ are of corresponding size.

As output to the constrained optimization it is desired to compute a constrained mask volume 50 which is indicated as M* and a constrained subtraction volume 52 which is indicated as S*. The constrained mask volume 50 also be described as a refined mask volume, since it constitutes a refinement of the initial predicted mask volume 42. The constrained subtraction volume 52 may also be described as a refined subtraction volume, since it constitutes a refinement of the initial predicted subtraction volume 44. The constrained mask volume 50 and constrained subtraction volume 52 may also be described as a final mask volume and final subtraction volume.

The first constraint is that the sum of the final prediction (M*) of the mask volume, constrained mask volume 50, and the final prediction (S*) of the subtraction volume, constrained subtraction volume 50, is equal to the original contrast volume 2, C, in every voxel. Index i is used to designate voxels.

$$C_i = M^*_i + S^*_i \forall_i \qquad \text{(Equation 1)}$$

It is desired that the constrained mask volume 50 and constrained subtraction volume 52 be as close to the predicted mask volume 42 and predicted subtraction volume 46 as possible, which were obtained without constraints being applied.

A variable $\sigma_i$ is introduced, where $\sigma_i \in [0,1]$. To obtain predictions that obey the first constraint, mask and subtraction intensities are written in terms of the new variable $\sigma_i$:

$$S^*_i = \sigma_i C_i$$

$$M^*_i = (1-\sigma_i)C_i \qquad \text{(Equation 2)}$$

The following constrained optimization problem may be written down. Solving the constrained optimization finds the closest possible mask volume and subtraction volume to the predicted mask volume 42 and predicted subtraction volume 46 that obeys the constraints:

$$\operatorname{argmin}_{\sigma_i} \left\| \begin{matrix} \sigma_i C_i - S_i^P \\ (1-\sigma_i)C_i - M_i^P \end{matrix} \right\|, \text{ subject to } 0 \le \sigma_i \le 1 \qquad \text{(Equation 3)}$$

In the present embodiment, the 2-norm is selected. In other embodiments, any suitable norm may be used.

Since the 2-norm is selected, the problem reduces to finding the minimizer of the following quadratic, with box constraints on $\sigma_i$:

$$f = (\sigma_i C_i - S_i^P)^2 + ((1-\sigma_i)C_i - M_i^P)^2 \qquad \text{(Equation 4)}$$

Since the leading coefficient of the quadratic is $2C_i^2 \ge 0$, the minimizer is unique and guaranteed to exist. An analytic solution may be derived. Take the derivative with respect to $\sigma_i$:

$$\frac{df}{d\sigma_i} = 2C_i(\sigma_i C_i - S_i^P) - 2C_i((1-\sigma_i)C_i - M_i^P) \qquad \text{(Equation 5)}$$

Setting Equation 5 to zero, simplifying, and applying the constraints gives:

$$\sigma_i = \min\left(1, \max\left(0, \frac{C_i + S_i^P - M_i^P}{2C_i}\right)\right) \quad \text{(Equation 6)}$$

Equation 6 is substituted back into Equation 2 to obtain a final constrained subtraction prediction and constrained mask prediction.

In the embodiment of FIG. 4, values of $\sigma_i$ are different for each voxel. All values of $\sigma_i$ are independent. In other embodiments, values of $\sigma_i$ may not be independent. Post-processing may be performed on determined values of 6l, for example to sharpen output or improve visualization.

Although a particular algorithm is described above, in other embodiments the algorithm may be different from that described. Any suitable algorithm may be used.

The optimization circuitry 36 outputs a constrained mask volume 50, M*, that has been obtained using the optimization procedure as described above. The optimization circuitry 36 outputs a constrained subtraction volume 52, S*, that has been obtained using the optimization procedure as described above.

The contrast volume 2, constrained mask volume 50 and constrained subtraction volume 52 are provided to the display circuitry 38. The display circuitry 38 performs a first display task 54 in which an image obtained from the contrast volume 2 is displayed to a user. For example, data of the contrast volume 2 may be rendered using any suitable rendering method and displayed to the user on display screen 26.

The display circuitry 38 performs a second display task 56 in which an image obtained from the constrained mask volume 50 is displayed to a user. For example, data of the constrained mask volume 50 may be rendered using any suitable rendering method and displayed to the user on display screen 26.

The display circuitry 38 performs a third display task 58 in which an image obtained from the constrained mask volume 52 is displayed to a user. For example, data of the constrained mask volume 52 may be rendered using any suitable rendering method and displayed to the user on display screen 26.

In other embodiments, any suitable combination of rendered images may be displayed to the user.

The method of FIG. 4 provides a method of maskless DSA. A contrast volume is obtained using rotational angiography. Using two trained models and an optimization procedure, DSA data is predicted from the rotational angiography data and may be used to visualize vascular pathology. The DSA is predicted from the contrast-enhanced volume without acquiring a mask. This may speed up the workflow and halve the radiation dose when compared with traditional subtraction methods in which both contrast data and non-contrast data are acquired. Mis-registration artefacts in the DSA may be prevented, since the DSA is predicted from the contrast volume without any registration of volumes being required. Motion artefacts may be eliminated.

Instead of using subtraction to generate a DSA volume from contrast and mask volumes, CNNs are trained to predict the mask and DSA volumes from a single contrast volume. The mask volume and the contrast volume are predicted independently. The two predictions are then combined by solving a constrained optimization problem. The constrained optimization procedure is intended to guarantee that when the final predicted mask and final predicted DSA are added, it results in the original measured contrast volume.

The optimization procedure of FIG. 4 may provide a number of improvements when compared to presenting the outputs of the CNNs 40, 44 without performing an optimization. Output of the CNNs 40, 44 without optimization may be described as the raw output of the CNNs 40, 44, and in the embodiment of FIG. 4 comprises the predicted mask volume 42 and the predicted subtraction volume 46.

Accuracy may be improved because the optimization may correct errors from one model. Combining two independent CNNs may improve accuracy because a mistake made by one CNN may be corrected by the other CNN.

Figure 1:
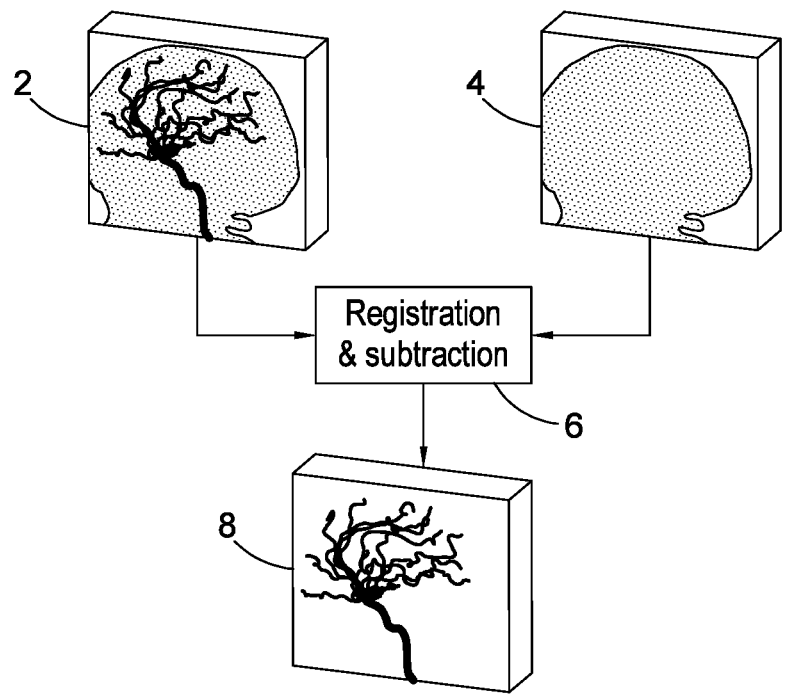
FIG. 1 is a flow chart illustrating in overview a digital subtraction method.
Figure 2:
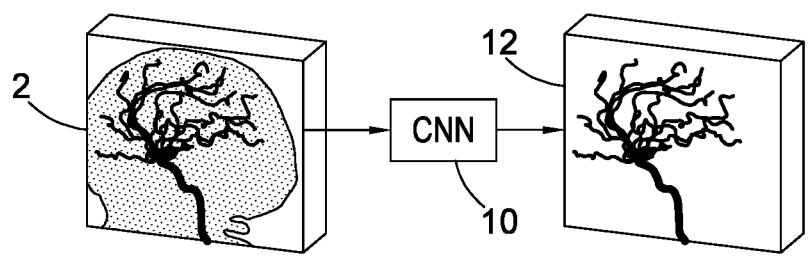
FIG. 2 is a flow chart illustrating in overview a method of predicting a DSA volume using a CNN.

Results may be easier to interpret. A possibility of the CNN introducing non-existent image structures to the subtraction volume or mask volume may be reduced or eliminated. The optimization may ensure that the observed attenuation coefficient in the contrast volume is conserved. A clinician may be more able to trust the output of the method of FIG. 4 than the output of a CNN alone (for example, an output of a method as shown in FIG. 2).

If mistakes are made by the CNNs, such mistakes may be very easy for a clinician viewing the results to interpret and understand. For example, if part of the vessel is not present in the constrained DSA, then it will be present in the constrained mask instead.

The embodiment of FIG. 4 uses a closed-form solution to the constrained optimization problem which may be extremely fast to compute, for example taking less than 1 second.

Figure 5:
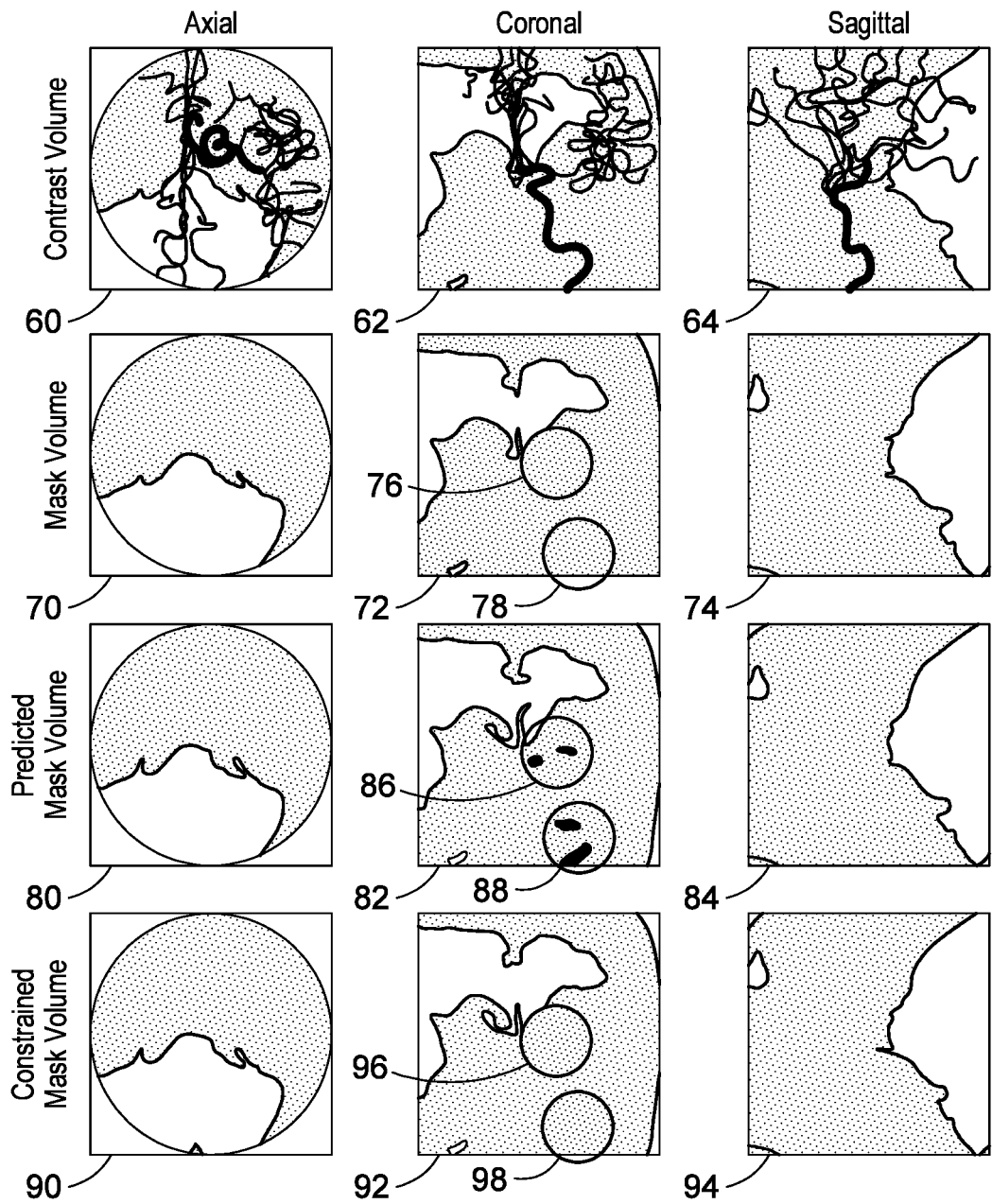
FIG. 5 comprises a plurality of images including contrast images, ground truth mask images, mask images predicted using a CNN, and mask images predicted by using a constrained optimization on predicted mask images.

FIG. 5 shows a plurality of axial, coronal and sagittal maximum intensity projection (MIP) views rendered from different volumes. A first set of images 60, 62, 64 comprises axial, coronal and sagittal views respectively of an input volume, which is a contrast volume. The input volume is obtained from a contrast-enhanced scan of an anatomical region. A second set of images 70, 72, 74 comprises axial, coronal and sagittal views respectively of a real (ground truth) mask volume obtained from a non-contrast scan of the same anatomical region. Circles 76, 78 in image 72 highlight two regions of interest in the real mask volume.

A third set of images 80, 82, 84 comprises axial, coronal and sagittal views respectively of a predicted mask volume. A 3D residual U-net was used to predict the mask volume from the contrast-enhanced volume used to obtain images 60, 62, 64. Circles 86, 88 in image 82 highlight the same regions of interest as are shown by circles 76, 78 in image 72. It may be seen that some sections of contrast-enhanced vessel are erroneously shown in the circles 86, 88 of image 82. It would not be possible for any contrast-enhanced vessel to be present in a real mask volume, so the presence of contrast-enhanced vessel in the predicted mask volume is clearly an error.

A fourth set of images 90, 92, 94 comprises axial, coronal and sagittal views respectively of a constrained mask volume which is an output of an optimization procedure as described above with reference to FIG. 4. The predicted mask volume used to obtain images 80, 82, 84 was combined with an independent DSA prediction (not shown in FIG. 5) in a constrained optimization. Circles 96, 98 in image 92 highlight the same regions of interest as are shown by circles 76, 78 in image 72 and circles 86, 88 in image 82. It may be seen that the parts of image 92 highlighted by the circles 96, 98 are more similar to image 72 than to image 82. The output of the constrained optimization is more similar to the real data than the output of the CNN without optimization. The constrained optimization may reduce or eliminate errors in the predicted mask volume.

In the embodiment of FIG. 4, the constraints are implemented mathematically as part of the optimization procedure. In other embodiments, constraints on the predicted subtraction volume and/or predicted mask volume may be implemented in any suitable manner. For example, in some embodiments, constraints may be implemented as part of a machine learning architecture.

In one embodiment, subtraction data and mask data are predicted by a CNN comprising a plurality of layers. One or more constraints are implemented in one or more layers of the CNN, so that the CNN outputs subtraction data and mask data to which the constraints have already been applied. The subtraction data and mask data that are output by the CNN already comply with the constraints, and may not require subsequent processing.

In other embodiments, any one or more trained models may be used to predict subtraction data and/or mask data, and the one or more constraints may be implemented in the one or more trained models in any suitable manner.

In the embodiment of FIG. 4, a mask CNN is used to predict the mask volume and a DSA CNN is used to predict the subtraction volume. The mask CNN and DSA CNN are independent of each other.

In other embodiments, a single trained model, for example a multi-head CNN, is used to predict both the mask volume and the subtraction volume. In some such embodiments, one or more constraints on the mask volume and subtraction volume are built into the multi-head CNN. Values for the variable a may be predicted within the CNN to give a further output of the CNN.

In some embodiments, two or more trained models are used to predict the subtraction volume. The trained models may be different types of trained model, for example different types of CNN. The models may be trained on different training data sets. The optimization circuitry 36 is configured to combine the outputs from the two or more trained models. The constrained optimization procedure is modified to accept two or more initial predictions of the subtraction volume from the two or more trained models. Similarly, in some embodiments, two or more trained models may be used to predict the mask volume. The constrained optimization procedure is modified to accept two or more initial predictions of the mask volume from the two or more models that are trained to predict the mask volume.

In some circumstances, some trained models may have difficulty in distinguishing between metal objects, which should be masked, and enhanced vessel, which should not be masked. Metal objects typically appear dark in the contrast volume. A trained model may be trained to classify all dark regions as vessel, which means that metal objects may also be incorrectly classified as vessel.

In some embodiments, the image processing circuitry 34 uses an additional trained model to segment metal objects in the contrast volume. Voxels of the segmented metal objects are labeled as metal. The optimization circuitry 36 then ensures that the metal objects appear in the constrained mask volume and do not appear in the constrained subtraction volume. For example, the optimization circuitry 36 may set $\sigma_i$ to 0 for each voxel that has been labeled as metal, meaning that the voxels labeled as metal only contribute to the predicted mask volume, and not to the predicted subtraction volume.

In embodiments described above, a contrast-enhanced volume is obtained by performing a scan of an anatomical region with contrast agent present, such that the contrast agent enhances the blood vessels in the anatomical region. The data obtained by the contrast-enhanced scan is then used to predict a mask volume in which contrast agent is not used, and a subtraction volume that represents a difference between the contrast-enhanced volume and the mask volume.

In other embodiments, any suitable method may be used to provide enhancement of blood in the anatomical region. Scan data of the anatomical region is obtained with the blood being enhanced. The data obtained in the scan having enhanced blood is then used to predict a mask volume in which no enhancement of blood is used, and subtraction volume that represents a difference between the contrast-enhanced volume and the mask volume.

In certain embodiments, there is provided a medical image processing apparatus comprising processing circuitry configured to: receive measured angiographic data; predict an unconstrained mask (non-enhanced) and subtraction (enhanced vessel only) image; and determine a final mask and subtraction prediction through solution of a constrained optimization problem such that voxel intensities are non-negative, and predicted mask and subtraction intensities sum to measured intensity in corresponding voxel.

Two CNNs may be used for initial prediction of subtraction and mask.

At least two CNNs may be used for initial prediction of subtraction and mask. The constrained optimization problem may be modified to accept multiple initial predictions.

A multi-head CNN may be used for initial prediction of subtraction and mask

The optimization objective may be the 2-norm of difference between predicted and constrained mask and subtraction.

The imaging modality may be 3D rotational angiography.

The imaging modality may be 2D fluoroscopy.

An additional CNN may be applied to segment metal objects in the contrast-enhanced volume, to ensure that metal objects are placed in the mask volume.

In certain embodiments, a medical image processing method comprises: receiving a set of angiography data that comprises or is obtained from scan data representing a volume that includes contrast agent; predicting, using a trained model, mask image data from the set of angiography data; predicting, using the trained model or a further trained model, subtraction image data from the same set of angiography data; refining the mask image data and the subtraction image data based on an optimization procedure subject to at least one constraint.

The at least one constraint may comprise ensuring that voxel intensities are non-negative. The at least one constraint may comprise ensuring that for each image location a sum of intensities of the predicted subtraction image data and the predicted mask image data correspond to an intensity for corresponding location(s) in the angiography data.

The mask image data may represent at least part of the volume without contrast agent. The mask image data may be predicted from the set of angiography data that comprises scan data representing the volume that does include contrast agent. The subtraction image data representing a subtraction of mask image data that includes contrast agent from image data that does not include contrast agent, and the subtraction image data may also be predicted from the set of angiography data that comprises scan data representing the volume that does include contrast agent.

A first convolutional neural network (CNN) may be used to predict the mask image data and a second CNN may be used to predict the subtraction image data.

The optimization procedure may be configured to accept multiple initial predictions.

A multi-head CNN may be used for initial prediction of the subtraction data and the mask data.

An objective of the optimization procedure may comprise optimization of a 2-norm of difference between predicted and constrained mask data and subtraction data.

The scan data may comprise 3D rotational angiography data.

The scan data may comprise 2D fluoroscopy data.

An additional CNN may be applied to segment metal objects to ensure that any metal objects are represented in the mask data.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments are described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus for producing constrained medical image data, the apparatus comprising:
   processing circuitry configured to:
      receive medical image data that comprises or is obtained from scan data representing an anatomical region in which a sub-region is enhanced;
      predict, using a trained model, mask data from the medical image data, wherein the mask data is representative of the anatomical region without enhancement of the sub-region; and
      predict, using the trained model or a further trained model, subtraction data from the same medical image data, wherein the subtraction data is representative of the same anatomical region, wherein
   each of the medical image data, the mask data, and the subtraction data comprises a respective intensity for each of a plurality of locations corresponding to a plurality of locations within the anatomical region, and
   the processing circuitry is further configured to apply at least two constraints to obtain constrained subtraction data, the at least two constraints comprising
      a first constraint ensuring that, for each of the plurality of locations, a sum of an intensity in the subtraction data and an intensity in the mask data corresponds to an intensity in the medical image data, and
      a second constraint ensuring that each of the intensities for each of the plurality of locations is non-negative.

2. The apparatus according to claim 1, wherein the applying of the at least two constraints comprises performing an optimization procedure based on the mask data and the subtraction data.

3. The apparatus according to claim 1, wherein the processing circuitry is further configured to obtain constrained mask data.

4. The apparatus according to claim 1,
   wherein the first constraint comprises ensuring that each of the intensities for each of the plurality of locations is within a predetermined range of intensity values.

5. The apparatus according to claim 1, wherein the applying of the at least two constraints comprises applying the at least two constraints within the trained model.

6. The apparatus according to claim 1, wherein the trained model comprises a plurality of layers and the applying of the at least two constraints comprises applying the at least two constraints using at least one layer of the plurality of layers.

7. The apparatus according to claim 1, wherein the applying of the at least two constraints is performed as part of the prediction of the mask data and/or the prediction of the subtraction data.

8. The apparatus according to claim 1, wherein a further trained model is used to predict the subtraction data.

9. The apparatus according to claim 1, wherein the trained model comprises a first convolutional neural network (CNN) and the further trained model comprises a second, independent CNN.

10. The apparatus according to claim 1, wherein the predicting of the mask data comprises using at least two different trained models and/or the predicting of the subtraction data comprises using at least two different trained models.

11. The apparatus according to claim 1, wherein the trained model comprises a multi-head CNN, and the trained model is used in the predicting of both the mask data and the subtraction data.

12. The apparatus according to claim 2, wherein the optimization procedure comprises finding a closest possible subtraction volume to the predicted subtraction volume that satisfies the at least two constraints, and designating the closest possible subtraction volume as the constrained subtraction volume.

13. The apparatus according to claim 2, wherein an objective of the optimization procedure comprises optimization of a 2-norm of a difference between predicted mask data and constrained mask data and a difference between predicted subtraction data and constrained subtraction data.

14. The apparatus according to claim 1, wherein the processing circuitry is further configured to:
   apply an additional trained model to the medical image data to obtain a segmentation of at least one metal object in the medical image data; and
   use the segmentation to ensure that the at least one metal object is represented in the mask data.

15. The apparatus according to claim 1, wherein the scan data represents the anatomical region with contrast agent present, the sub-region is enhanced in the medical image by presence of the contrast agent, and the mask data is representative of the anatomical region without the contrast agent.

16. The apparatus according to claim 1, wherein the scan data comprises at least one of 3D rotational angiography data, 2D fluoroscopy data, CT data, MR data.

17. The apparatus according to claim 1, wherein the scan data is obtained from a cone-beam C-arm acquisition.

18. A method for producing constrained medical image data, the method comprising:
   receiving medical image data that comprises or is obtained from scan data representing an anatomical region in which a sub-region is enhanced;

predicting, using a trained model, mask data from the medical image data, wherein the mask data is representative of the anatomical region without enhancement of the sub-region;

predicting, using the trained model or a further trained model, subtraction data from the same medical image data, wherein the subtraction data is representative of the same anatomical region, and each of the medical image data, the mask data, and the subtraction data comprises a respective intensity for each of a plurality of locations corresponding to a plurality of locations within the anatomical region; and applying at least two constraints to obtain constrained subtraction data, the at least two constraints comprising
a first constraint ensuring that, for each of the plurality of locations, a sum of an intensity in the subtraction data and an intensity in the mask data corresponds to an intensity in the medical image data, and
a second constraint ensuring that each of the intensities for each of the plurality of locations is non-negative.

19. The apparatus according to claim 1, wherein the processing circuitry is configured to:

receive medical image data that comprises or is obtained from scan data representing an anatomical region in which a sub-region is enhanced by presence of a contrast agent;

produce, using the trained model, mask data from the medical image data, wherein the mask data includes bone and/or soft tissue and is representative of the anatomical region without enhancement by the presence of the contrast agent in the sub-region;

produce, using the trained model or the further trained model, subtraction data from the same medical image data, wherein the subtraction data is representative of the same anatomical region and excludes the bone and/or soft tissue but includes the sub-region where the contrast agent is present; and apply the at least two constraints to the subtraction data and the mask data to obtain constrained subtraction data.

* * * * *